United States Patent
Jeng

(10) Patent No.: US 10,973,534 B2
(45) Date of Patent: Apr. 13, 2021

(54) TISSUE TRAP FOR CHONDRAL AUTOGRAFT TRANSFER SYSTEM

(71) Applicant: Smith & Nephew, Inc., Memphis, TN (US)

(72) Inventor: Lily Jeng, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 161 days.

(21) Appl. No.: 15/761,660

(22) PCT Filed: Nov. 21, 2016

(86) PCT No.: PCT/US2016/063055
§ 371 (c)(1),
(2) Date: Mar. 20, 2018

(87) PCT Pub. No.: WO2017/091498
PCT Pub. Date: Jun. 1, 2017

(65) Prior Publication Data
US 2018/0344327 A1 Dec. 6, 2018

Related U.S. Application Data

(60) Provisional application No. 62/259,945, filed on Nov. 25, 2015, provisional application No. 62/325,083, (Continued)

(51) Int. Cl.
*A61B 17/16* (2006.01)
*A61M 1/00* (2006.01)
(Continued)

(52) U.S. Cl.
CPC ........ *A61B 17/1659* (2013.01); *A61B 10/025* (2013.01); *A61B 17/1635* (2013.01);
(Continued)

(58) Field of Classification Search
CPC ............ A61M 1/0056; A61B 17/1635; A61B 17/1659; A61B 10/025
See application file for complete search history.

(56) References Cited

U.S. PATENT DOCUMENTS

| 5,683,406 A | 11/1997 | Altobelli et al. |
| 5,871,493 A * | 2/1999 | Sjostrom .............. A61B 17/162 604/22 |

(Continued)

OTHER PUBLICATIONS

International Search Report and Written Opinion for International Application No. PCT/US2016/063055, dated Feb. 13, 2017, 12 pages.

(Continued)

*Primary Examiner* — Olivia C Chang
(74) *Attorney, Agent, or Firm* — Burns & Levinson, LLP; Joseph M. Maraia

(57) ABSTRACT

A cartilage repair technique employs a cutter-tissue trap combination device to harvest cartilage tissue from a low-weight-bearing site of a subject. Cut tissue is aspirated though a lumen (1101) of a tissue cutter (1100). The lumen includes an outer shaft (1106) having a first distal window and an inner shaft having a second distal window. Edges of the first distal window and the second distal window cooperate to provide a cutting action there-between upon rotation of the inner shaft within the outer shaft. A tissue trap (1400) coupled to the tissue cutter is configured to collect tissue shavings of a desired size to efficiently deliver the collected shavings to a repair site during surgery. The tissue trap includes a filter (1502) in a housing configured between a removable inflow chamber (1404) and a removable outflow chamber (1406).

7 Claims, 12 Drawing Sheets

Related U.S. Application Data filed on Apr. 20, 2016, provisional application No. 62/328,148, filed on Apr. 27, 2016.

(51) Int. Cl.
  *A61B 10/02* (2006.01)
  *A61B 17/32* (2006.01)
  *A61B 17/00* (2006.01)
  *A61B 17/3207* (2006.01)

(52) U.S. Cl.
  CPC ....... *A61M 1/0056* (2013.01); *A61B 10/0283* (2013.01); *A61B 17/32002* (2013.01); *A61B 17/320708* (2013.01); *A61B 2017/00477* (2013.01); *A61B 2017/00969* (2013.01); *A61B 2217/005* (2013.01); *A61B 2217/007* (2013.01); *A61M 2202/095* (2013.01)

(56) References Cited

U.S. PATENT DOCUMENTS

| | | | | |
|---|---|---|---|---|
| 6,299,763 | B1* | 10/2001 | Ashman | A61C 1/0076 210/448 |
| 2002/0161449 | A1* | 10/2002 | Muschler | A61L 27/365 623/23.51 |
| 2003/0130594 | A1 | 7/2003 | Hynes et al. | |
| 2004/0193071 | A1* | 9/2004 | Binette | A61F 2/4644 600/562 |
| 2008/0243028 | A1* | 10/2008 | Howard | A61B 17/3205 600/565 |
| 2017/0049930 | A1 | 2/2017 | Nasert et al. | |

OTHER PUBLICATIONS

European Application No. 16809260.9-1122 Examination Report dated Dec. 19, 2019.

* cited by examiner

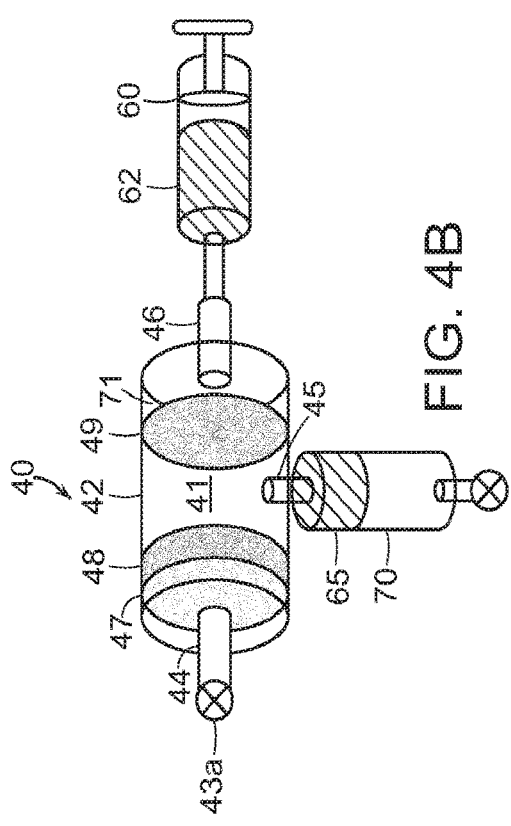
FIG. 4A
FIG. 4B
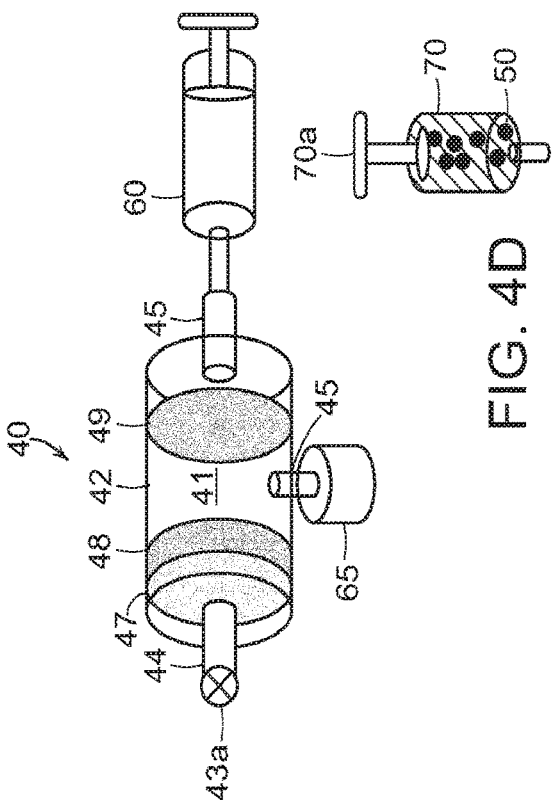
FIG. 4D
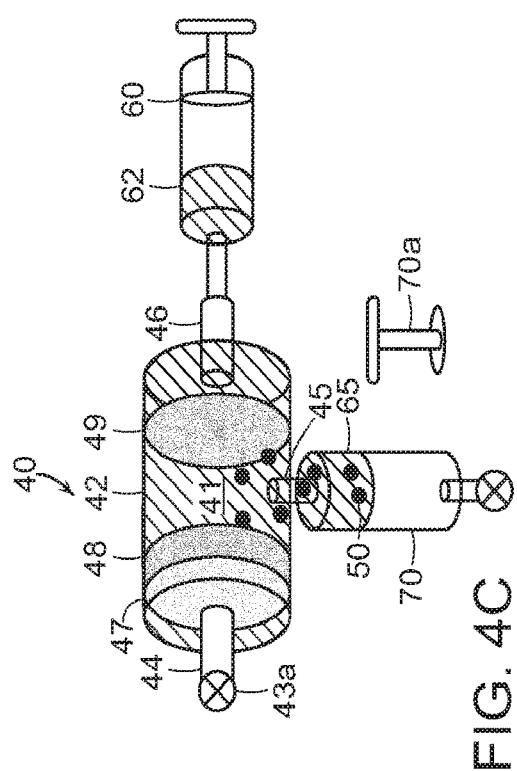
FIG. 4C

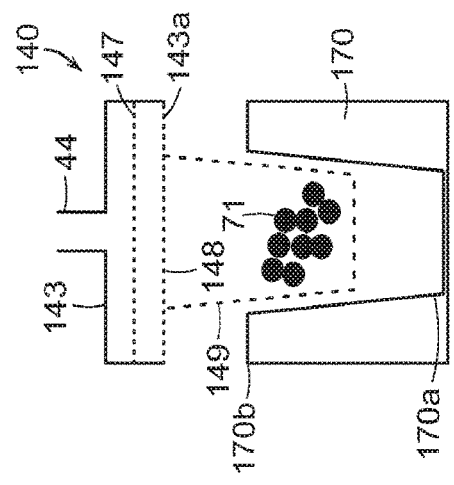
FIG. 7A
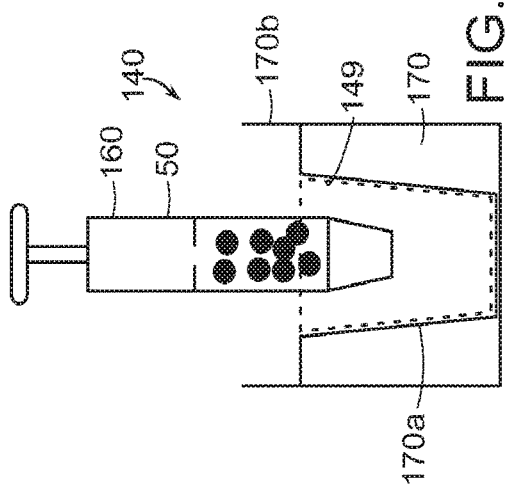
FIG. 7B
FIG. 7C
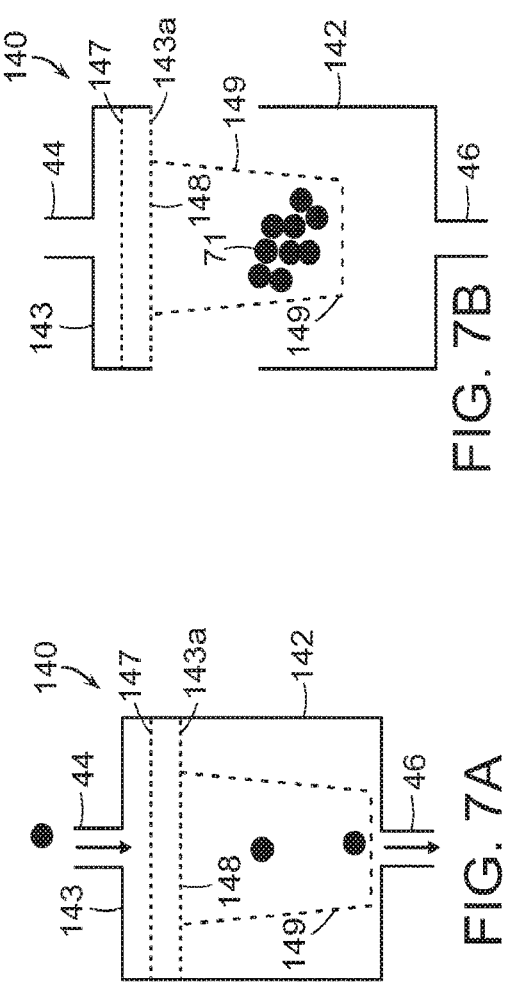
FIG. 7D
FIG. 7E
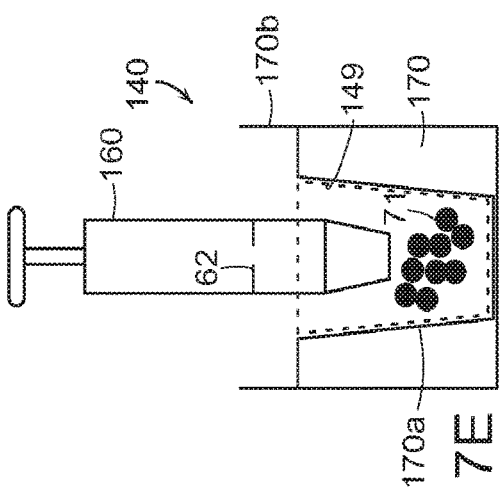
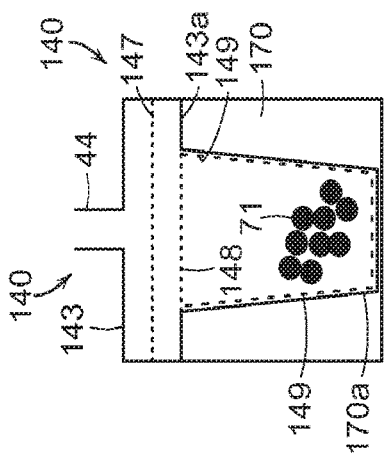
FIG. 7F

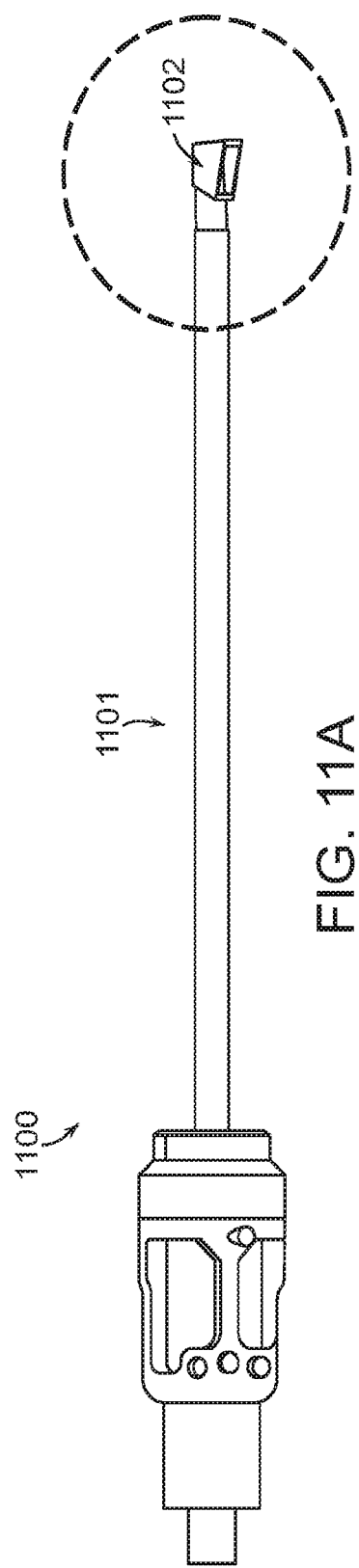
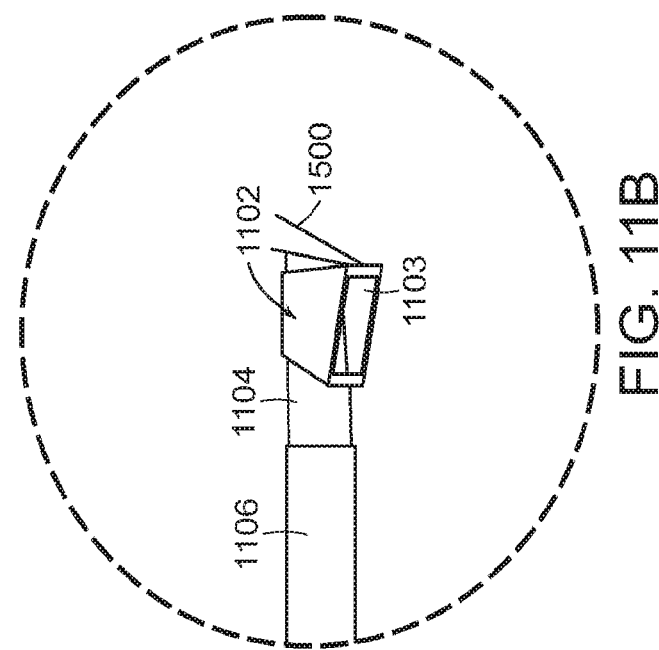

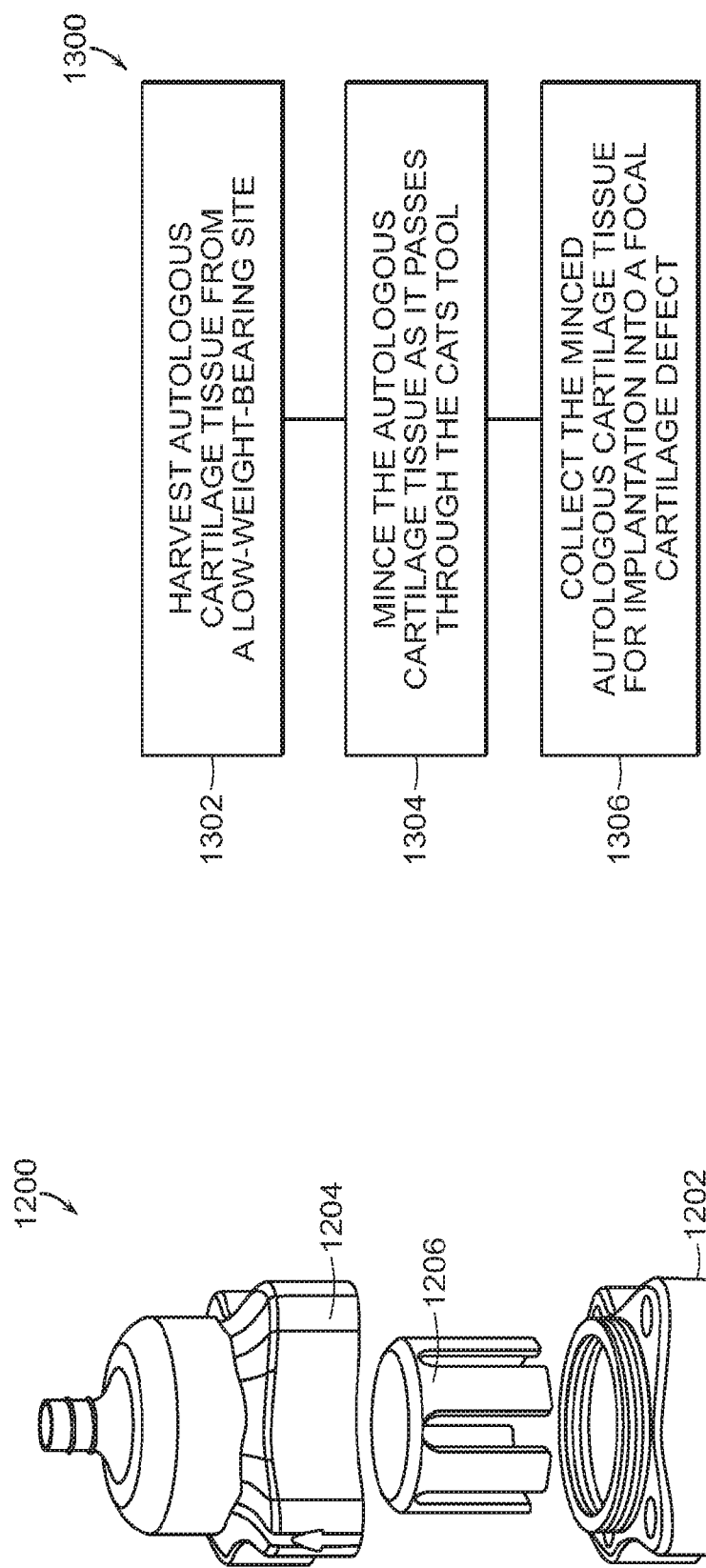

TISSUE TRAP FOR CHONDRAL AUTOGRAFT TRANSFER SYSTEM

CROSS REFERENCE TO RELATED APPLICATIONS

This application is the U.S. national phase entry under 35 U.S.C. § 371 of International Application No. PCT/US2016/063055, filed Nov. 21, 2016, entitled TISSUE TRAP FOR CHONDRAL AUTOGRAFT TRANSFER SYSTEM, which in turn claims priority to and benefit of U.S. Provisional Application No. 62/259,945, entitled TISSUE TRAP FOR CHONDRAL AUTOGRAFT TRANSFER SYSTEM which was filed on Nov. 25, 2015, the contents of which are incorporated herein by reference in their entirety. The present application also claims priority to U.S. Provisional Patent Application No. 62/325,083 entitled TISSUE TRAP FOR CHONDRAL AUTOGRAFT TRANSFER SYSTEM which was filed on Apr. 20, 2016, the contents of which are incorporated herein by reference in their entirety. The present application also claims priority to U.S. Provisional Patent Application No. 62/328,148 entitled TISSUE TRAP FOR CHONDRAL AUTOGRAFT TRANSFER SYSTEM which was filed on Apr. 27, 2016, the contents of which are incorporated herein by reference in their entirety.

TECHNICAL FIELD

The present disclosure relates to tissue harvesting.

BACKGROUND

Articular cartilage is an avascular, aneural, alymphatic tissue, which lines the ends of bones and facilitates frictionless movement of joints. Damage to the cartilage caused by injury or disease does not heal and the pathological changes resulting from this damage can be a source of great pain; limiting mobility and having a significant detrimental impact on the quality of life. Over time, lesions are likely to degenerate into osteoarthritis. Injury is not the only cause of osteoarthritis, with genetics, obesity, joint biomechanics, diet and age all playing a role. Focal chondral defects present a significant clinical challenge, as they are a common source of pain and can lead to a decrease in mobility and the onset of osteoarthritis.

Known surgical techniques for treating damaged cartilage comprise lavage and debridement (joint is flushed with fluid and damaged tissue removed providing temporary symptom relief); microfracture (penetration of the subchondral bone to stimulate bleeding in to the cartilage lesion in an effort to promote a fibrocartilage healing response); periosteal grafts (autologous periosteum is grafted into the defect site and sutured or glued into place); mosaicplasty (plugs of cartilage and bone are harvested from low weight bearing regions of the joint and transplanted into the defect); and autologous chondrocyte implantation (ACI) (cells are isolated and expanded from a cartilage biopsy from a non-weight bearing location, and the cells are re-introduced into the defect in a second procedure approximately six weeks later either in suspension or on a scaffold (Matrix-guided ACI-MACI)).

Some of the previously known surgical techniques may involve separate surgical procedures that occur on two different days. Moreover, clinical results of some of the previously known surgical techniques suggest that the long-term biochemical and biomechanical properties of the reparative tissue are generally not satisfactory.

SUMMARY

The tissue harvesting techniques described below can be used to repair, regenerate, and/or augment tissue in a range of surgical or cosmetic applications.

Trauma to the articular surface is a common injury in sports. The symptoms arising from such damage comprise pain, joint locking, instability, and stiffness. The damage predisposes the cartilage and joint to wear and degeneration which can lead to osteoarthritis and the need for total knee replacement. For example, the tissue harvesting techniques can be used to treat focal and degenerative cartilage lesions before a total joint replacement is indicated and can postpone or obviate the need for a total joint replacement. The techniques enable the surgical team to purify a unique population of repair cells from tissue from the patient, such as, for example, synovial/adipose tissue, and deliver the cells back into the patient's joint to stimulate a hyaline-like cartilage repair in a single surgical procedure. The repair cells are harvested arthroscopically from a site local to the defect (i.e. within the joint), the repair cells of a desired range are isolated, for example, by filtering, and the isolated cells are mixed in an unprocessed state (e.g., without further culturing, concentrating, etc.) with a biocompatible gel. The mixture of gel and the isolated harvested cells is then provided to the repair site.

In implementations of the disclosure the adipose tissue harvested is a fat pad or corpus adiposum, which is a localized accumulation of encapsulated adipose tissue. Fat pads can be found, for example in the cheek (corpus adiposum buccae) and also found within certain joints where they are referred to as the infrapatellar, navicular, olecranon, scaphoid, pronator quadratus, and preachilles fat pads. These pads may act as a cushion to absorb forces generated across the joint and also may help to distribute lubricants in the joint cavity.

The infrapatellar fat pad, also referred to as Hoffa's pad and adipose synovium, comprises synovium and subsynovial adipose tissues and lies beneath the patella (kneecap) separating it from the femoral condyle. The infrapatellar fat pad varies in size and volume, but generally comprises two large basal prominences lying on either side of the intrachondylar notch. In situations where forces are directed at the patella, the infrapatellar fat pad acts as a shock absorber, protecting the underlying structures. During trauma the infrapatellar fat pad undergoes a number of changes, which comprise, without limitation, the fat pad volume increasing secondary to oedema and haemorrhage due to increased subsynovial vascularisation and the subsequent infiltration of the fat pad with macrophages.

We have found that by harvesting a defined size fragment of fat pad tissue, comprising progenitor cells, and reintroducing this fragment in combination with a biocompatible scaffold, such as a gel, into another site within the body, it is possible to generate tissue types that are different from the tissue fragment following exposure of the fragment to environmental factors.

It is envisaged that the progenitor cells contained within the fragments of fat pad could be directed along, for instance, the osteogenic, adipogenic, chondrogenic, myogenic, neurogenic lineages giving rise to bone, cartilage, muscle or nerve tissue.

Once the fat pad fragments are implanted into the site, the progenitor cells migrate out of the fragments and integrate into the surrounding tissue, thereby allowing the progenitor cells to differentiate into the appropriate endogenous cell type(s).

The fat pad tissue can be autogeneic tissue, allogeneic tissue, xenogeneic tissue and combinations thereof.

The use of autogeneic tissue is particularly desirable as it substantially reduces the potential for an immunogenic host response and tissue rejection.

If autogenic fat pad is to be used, a specific consideration for the surgeon is how readily accessible the fat pad is during the primary surgical procedure. For example, if a surgeon is repairing a cartilage defect within the femoral plateau, then it would be appropriate to use the infrapatellar fat pad. This will minimise the incisions that the surgeon has to make and therefore improve the outcome and the welfare of patient.

Using autologous tissue as a source for cartilage repair implants is often limited due to a number of problems including: availability, source, pain and enrichment. The infrapatellar fat pad is a joint tissue that is easily accessible to the orthopedic surgeon and is present in sufficient quantity to load a number of scaffolds for use in cartilage repair, particularly of focal defects. Furthermore, the use of the infrapatellar fat pad substantially reduces the possibility of secondary site morbidity when compared to other tissue sources, such as bone marrow aspirations, and substantially reduces the need to enrich the progenitor cells to show therapeutic effect.

In one aspect, the present disclosure relates to an apparatus for tissue collection comprising: a housing defining an inlet and an outlet; a first filter disposed within the housing; a second filter disposed within the housing, the second filter configured to isolate tissue particles of a desired size that pass through the first filter under the application of an aspiration force applied through the housing.

Implementations may comprise one or more of the following features. For example, the apparatus further comprises a third filter disposed in the housing between the first and second filters. The second filter is configured to isolate tissue particles of a desired size that pass through the first and third filters under the application of the aspiration force applied through the housing. The first and second filters disposed within the housing define an interior space within the housing, wherein the apparatus further comprises a port disposed within the housing and in fluid-flow communication with the interior space defined within the housing. The apparatus further comprises an introducer configured to comprise a gel. The introducer is configured to be coupled to the outlet of the housing to introduce the gel into the interior space of the housing, such that in use, the gel passes through the second filter and removes isolated tissue particles collected on the second filter, and wherein the gel and isolated tissue particles collect in the interior space of the housing. The apparatus further comprises a mixer and a receiver. The mixer and the receiver are configured to be releasably coupled to the port to receive the gel and isolated tissue particles from the interior space of the housing. The first filter comprises a set of pores having a pore size of about 0.6 mm to about 2.4 mm, the second filter comprises a set of pores having a pore size of about 0.5 mm to about 50 .mu.m, and the third filter comprises a set of pores having a pore size of about 0.6 mm to about 1 mm. The apparatus further comprises a fluid-flow conduit in the interior space of the housing and in fluid-flow communication with the inlet and the outlet. The apparatus further comprises a second port disposed in the housing. The first port and the second port are in fluid-flow communication with the conduit. The apparatus further comprises a first valve and a second valve, the first and second valves configured to allow for selective control of fluid flow between the inlet and the outlet and the first and second ports. The inlet is in fluid communication with a surgical blade and the outlet is in fluid communication with an aspiration source.

In an embodiment, the housing comprises a removable lid. The first filter is disposed within the lid. The third filter is disposed within the lid between the first filter and the second filter. The second filter comprises a basket mesh or a substantially frusto-conical configuration. The second filter is releasably coupled to the housing or the lid. The apparatus further comprises a container shaped to receive the second filter therein upon removal of the second filter from the housing.

In another aspect, the present disclosure relates to a method of harvesting tissue comprising isolating particles of a desired range from cut tissue aspirated through a tissue cutter, mixing the isolated particles in an unprocessed state with a biocompatible gel, and collecting the mixed particles and gel in an introducer for implantation into a surgical site.

Implementations may comprise one or more of the following features. For example, isolating the particles of a desired range comprises passing the cut tissue through a first filter and a second filter. The second filter comprises openings sized to permit collection of the particles of the desired range on the second filter. The method further comprises passing the biocompatible gel through the second filter to remove isolated particles collected on the second filter prior to mixing the isolated particles with the biocompatible gel. Mixing the isolated particles and the gel comprises passing the isolated particles and gel through a mixer coupled to the introducer Mixing the isolated particles and the gel also comprises placing the second filter with the collected particles in a container configured to receive the second filter therein and introducing the biocompatible gel into the container. The collecting step comprises aspirating the mixed isolated particles and the gel from the container into the introducer. The cut tissue is synovial or adipose tissue. The isolating step comprises collecting particles of the desired range in a filter of a tissue collection device solely under the application of an aspiration force applied through the tissue collection device to the aspiration lumen of the tissue cutter to aspirate tissue therethrough.

Advantages may comprise eliminating the risk of disease transmission and immune response associated with treatment using allograft; enabling cartilage repair procedures to be performed in focal lesions in older as well as young patients; minimizing damage to the donor site; isolating tissue fragments which are within a specific size range; minimizing intervention from the surgeon; and harvesting tissue, loading tissue within a gel in an expedient manner, and providing the tissue-containing gel for tissue repair in a sterile manner in a single surgical procedure.

The details of one or more embodiments of the disclosure are set forth in the accompanying drawings and the description below. Other features, objects, and advantages of the disclosure will be apparent from the description and drawings, and from the claims.

Aspects of the present disclosure address deficiencies of typical cartilage repair techniques such as cell-based implantations and scaffold-based or matrix-based implantations, in which reparative tissue are generally not satisfactory, and which may involve multiple surgical procedures.

The disclosed cartilage repair technique employs a shaver-cutter-tissue trap combination device to harvest cartilage tissue form a low-weight-bearing site of a subject. Tissue is resected by the shaver blade and then aspirated though a lumen of a tissue cutter. The lumen includes an outer shaft having a first distal window and an inner shaft having a second distal window. Edges of the first distal window and the second distal window cooperate to provide a cutting action there-between upon rotation of the inner shaft within the outer shaft. The shaver blade is formed on a curette extending from the outer shaft around the first window.

A tissue collection apparatus is coupled in the aspiration path of the cutting via flexible aspiration tubing. The tissue collection apparatus includes a filter portion having pores, which are sized to allow tissue particles that are below a desired size to pass through and aspirated as waste tissue from the device. Tissue particles having desired size are collected in the filter portion. In an embodiment, the tissue collection apparatus may include a two-part housing that can be opened during surgery to remove the filter portion and access the collected tissue particles. The collected cartilage tissue particles can then be introduced to the cartilage repair site of the subject during the surgery and secured to a cartilage defect, possibly by using a fibrin glue.

Use of disclosed method and apparatus reduces the need for multiple surgeries and also facilitates improved long-term biochemical and biomechanical properties of the reparative tissue by efficiently harvesting and implanting autologous tissue during a single surgical procedure.

According to an aspect of the present disclosure, an apparatus for tissue collection includes an outer shaft having a distal end and a proximal end, and having a longitudinal axis. The outer shaft includes a first window in an area of the distal end. The outer shaft includes at least one cutting edge. A hollow inner shaft is received in the outer shaft. The hollow inner shaft has at its distal end at least one opening that includes at least one cutting edge cooperating with the at least one cutting edge of the first window in a cutting action when rotating the inner hollow shaft relative to the outer shaft about the longitudinal axis. According to an aspect of the present disclosure, the first window is at least partially surrounded by a curette portion. In an illustrative embodiment, the curette portion fully surrounds the first window. The curette portion includes a separating edge for separating tissue and cartilage from the body by penetrating the separating edge into the tissue. The curette portion allows for cutting soft tissue, such as cartilage, which is then aspirated into the shaft. While the soft tissue is being aspirated, the outer window and inner window cooperate to mince the pieces of the soft tissues that are being collected.

BRIEF DESCRIPTION OF DRAWINGS

FIGS. 4a-4d schematically illustrate use of the tissue collection apparatus of FIG. 3 to isolate tissue particles of a desired size and to prepare a mixture of tissue-containing gel for tissue repair.

FIGS. 7a-7f schematically illustrate use of the tissue collection apparatus of FIG. 6 to isolate tissue particles of a desired size and to prepare a mixture of tissue-containing gel for tissue repair.

FIGS. 11A and 11B are illustrations of a cutter and scraper portion of a tissue harvesting tool according to an aspect of the present disclosure.

FIG. 12 is an illustration of a tissue collector portion of the tissue harvesting tool according to an aspect of the present disclosure.

FIG. 13 is a process flow diagram illustrating a method for harvesting tissue according to an aspect of the present disclosure.

DETAILED DESCRIPTION

Figure 1:
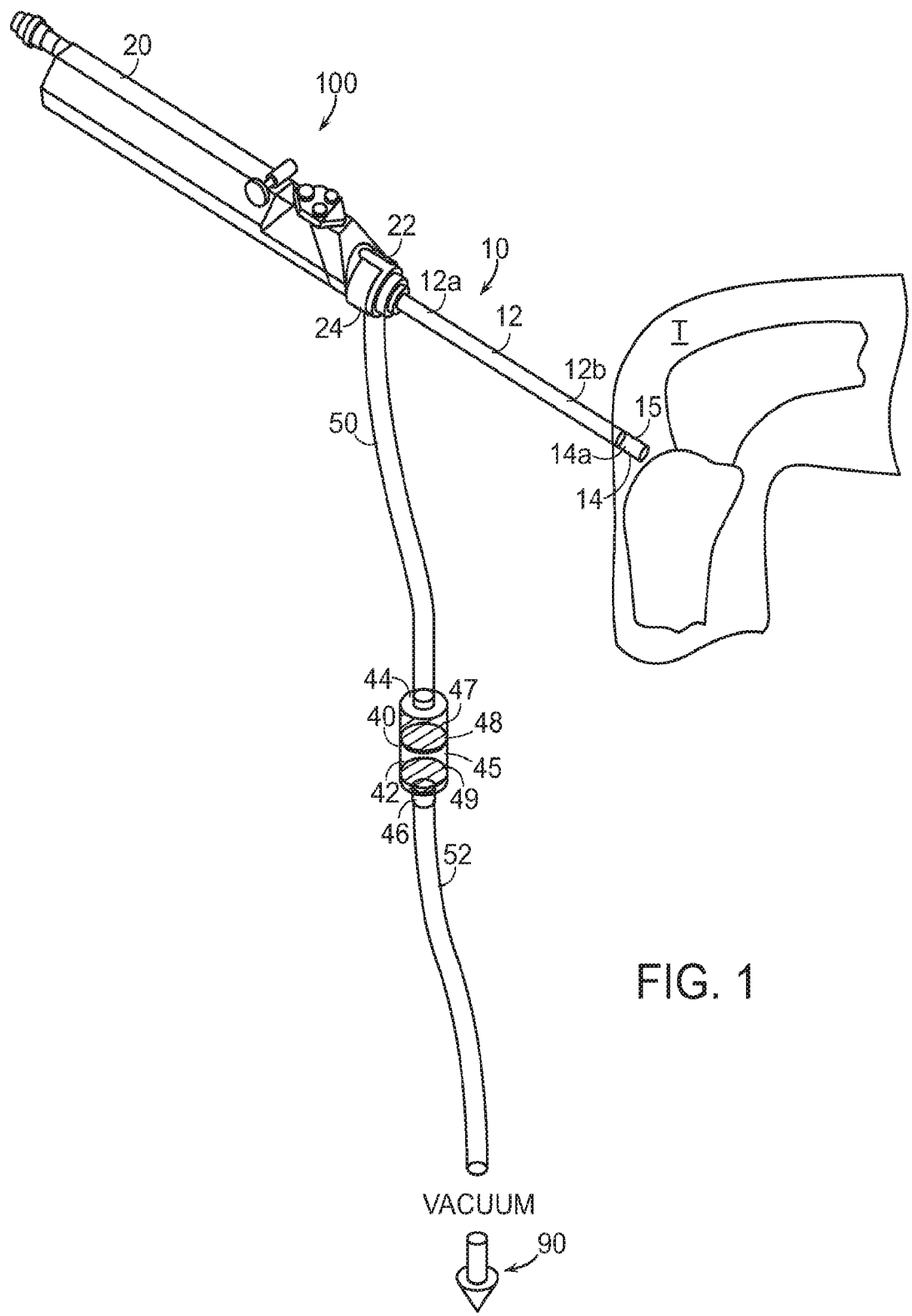
FIG. 1 is an illustration of a tissue harvesting assembly shown in use.

Referring to FIG. 1, a tissue harvesting assembly 100 comprises a surgical blade 10 used to cut or resect bodily tissue T, such as synovial or adipose tissue, from a donor site, coupled to a tissue collection device 40 for isolating cut tissue of a desired size aspirated through the surgical blade 10. As discussed below, during the same surgical procedure, the isolated cut tissue is loaded into, or mixed with, an appropriate carrier, such as a biocompatible gel, and introduced at a tissue repair site. Preferably, the donor site and the repair site are within the same joint to minimize trauma to the patient and provide for a more expedient surgical procedure.

Surgical blade 10 uses a tube-in-tube construction to shear tissue disposed between cutting edges of an elongate outer non-rotating tubular member 12 and an elongate inner rotating tubular member 14, as more fully explained in U.S. Pat. No. 5,871,493, which is incorporated herein by reference in its entirety. The surgical blade 10 comprises a handpiece 20 coupled to the tubular members 12, 14 via a hub 22. The outer tubular member 12 has a proximal end 12a fixed to the hub 22 and a distal end 12b defining an opening 15 forming a cutting port or window. The inner tubular member 14 is rotatably received in the outer tubular member 12 and has a distal end 14a with a cutting edge (not shown). The inner tubular member 14 defines an aspiration lumen 16 (FIG. 2) communicating with the cutting edge to remove cut tissue and fluid from a surgical site. When the blade 10 is assembled, the cutting edge of the inner tubular member 14 is positioned adjacent the opening 15 of the outer tubular member 12.

Figure 2:
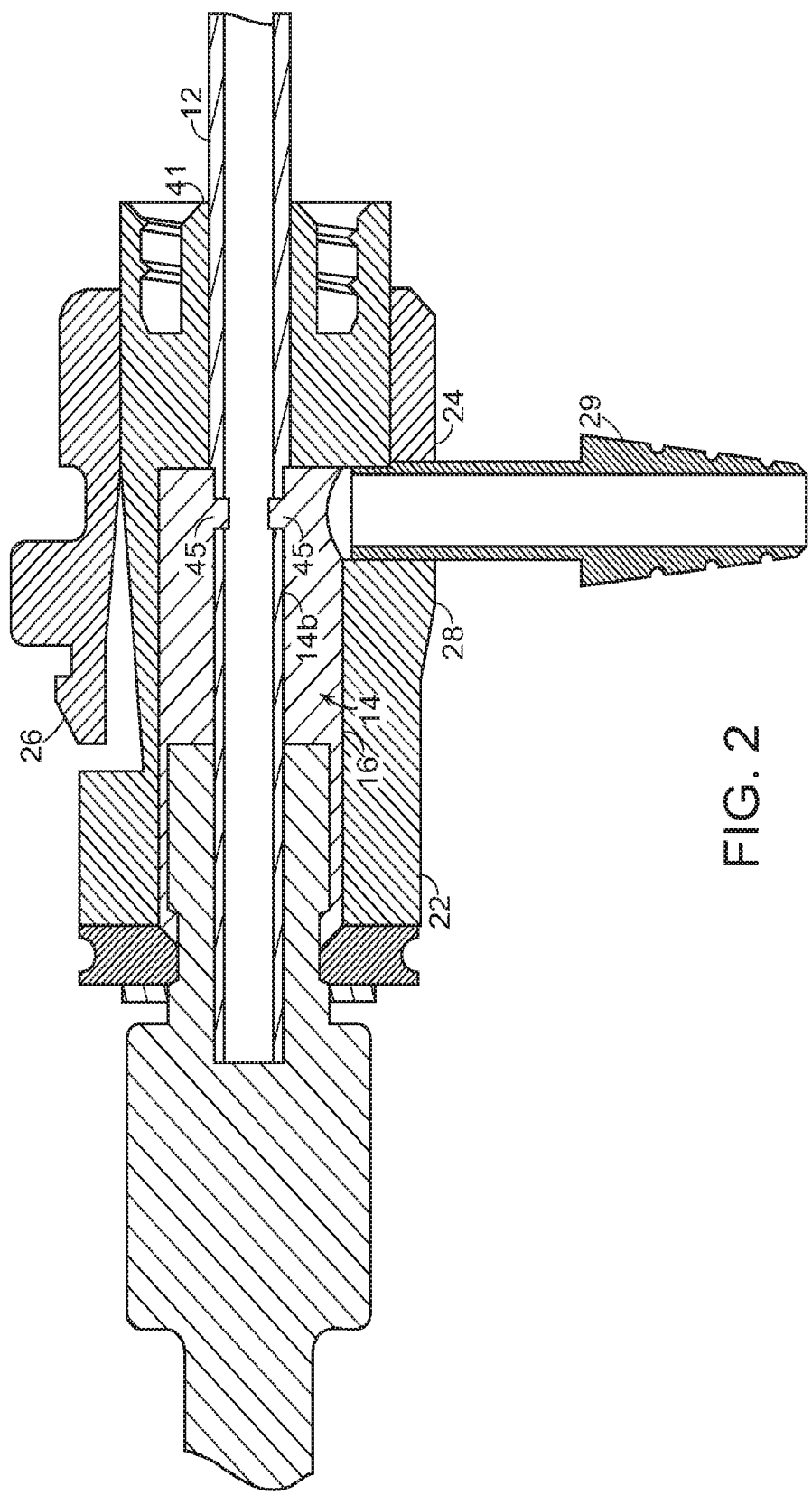
FIG. 2 is a cross-sectional view of the surgical blade hub of the assembly of FIG. 1.
Figure 3:
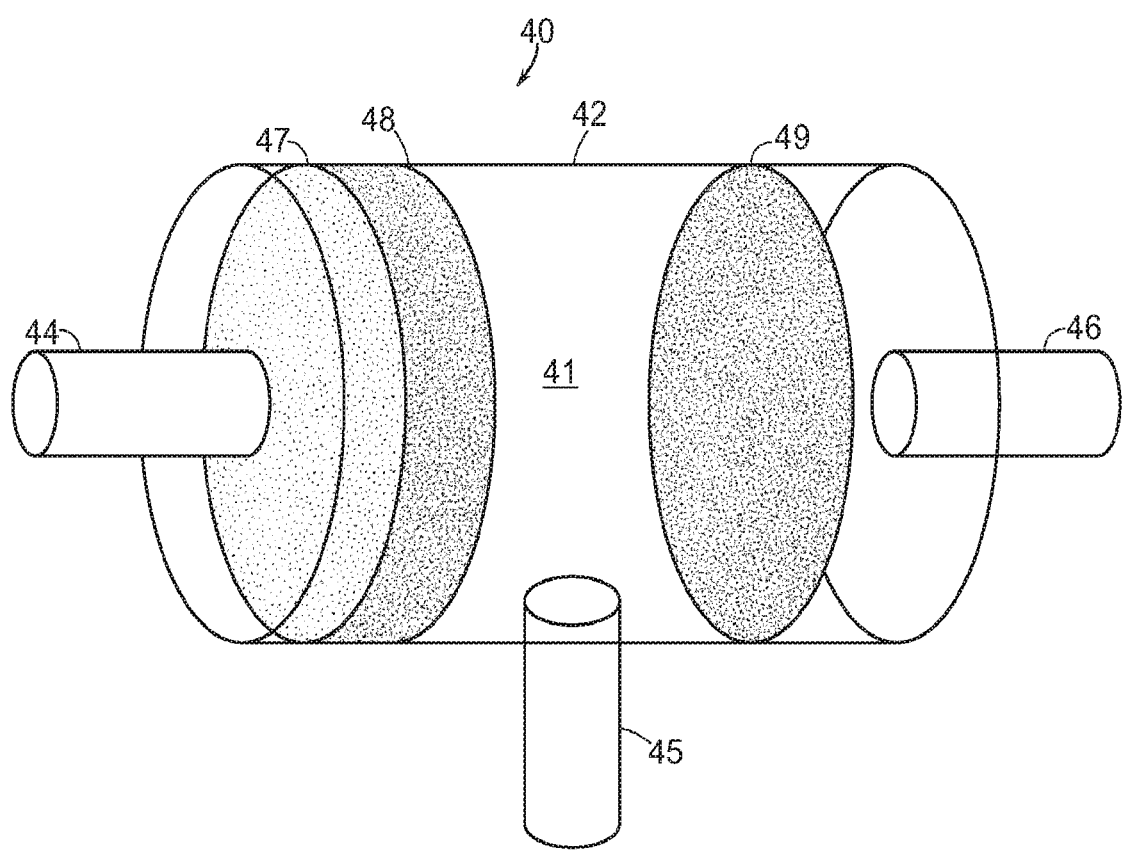
FIG. 3 is a perspective view of a tissue collection apparatus of the assembly of FIG. 1.

Referring to FIG. 2, the hub 22 (FIG. 1) of the surgical blade 10 is coupled to the outer tubular member 12 via an opening 41 formed in the hub 22. The inner tubular member 14 is rotatably received within the outer tubular member 12 and defines the aspiration lumen 16 extending longitudinally through the inner tubular member 14. The inner tubular member 14 further defines one or more openings 45 formed through a side wall 14b of the member 14 within the hub region of the blade 10, which are in fluid communication with the aspiration lumen 16 and a chamber 26 defined within hub 22. Hub 22 further comprises a side port 24 formed through a side wall 28 of hub 22 and in fluid communication with the chamber 26. The side port 24 extends in a direction substantially transverse to the longitudinal axis L of the inner tubular member 14. Coupled to the side port 24 is a tubing connector 29. The side port 24 provides a pathway for fluid and cut tissue to flow from the surgical blade 10 to the tissue collection device 40.

Referring to FIGS. 1, 3, and 4A-4D, in addition to the tissue collection device 40, the tissue harvesting assembly 100 comprises an introducer 60 (FIGS. 4B-4D) and a mixer 65 (FIGS. 4B-4D). The tissue collection device 40 is coupled to the blade 10 via a flexible tubing 50. The tissue collection device 40 comprises a substantially cylindrical housing 42 having an inlet 44 and an outlet 46. The inlet 44 couples the tubing 50 to the tissue collection device 40. The outlet 46 is provided to couple the tissue collection device 40 to a source of vacuum 90 (FIG. 1), such as a vacuum pump or other suitable apparatus for providing aspiration during the surgical procedure, via a tubing 52. In addition, a collection apparatus (not shown) can be coupled to the tissue collection device 40 via the tubing 52 to collect tissue and fluid that passes through the tissue collection device 40.

Filtration devices, such as disc filters 47, 48, and 49, are positioned within the housing 42 with filter 47 disposed closest to or adjacent the inlet 44, filter 49 disposed closest to or adjacent the outlet 46, and filter 48 disposed between filters 47 and 49. The filters 47, 48, and 49 and the housing 42 cooperate to define an interior space 41 within the housing 42. The housing 42 comprises a port 45 disposed therein, which is in fluid-flow communication with the interior space 41 of the housing 42.

In the implementation shown in FIGS. 1, 3, and 4A-4D, the filter 47 comprises a set of pores having a pore size of about 0.6 mm to about 2.4 mm, the filter 48 comprises a set of pores having a pore size of about 0.6 mm to about 1 mm, and the filter 49 comprises a set of pores having a pore size of about 0.5 mm to about 50 μm. The filters 47 and 48 filter out larger tissue particles and allow smaller particles to pass through. The filter 49 then filters out particles 71 (FIG. 4B) of a desired size and allow particles smaller than the desired size to pass through. While two filters 47, 48 are shown in this implementation, the tissue collection device 40 may comprise only one of the filters 47, 48 used in conjunction with the filter 49 to collect tissue particles 71 of a desired size.

The introducer 60 (FIGS. 4B-4D), for example, a syringe, contains a suitable volume (e.g., about 1 ml) of a biocompatible gel 62. After particle collection, the syringe 60 is used to inject the biocompatible gel 62 into the housing 42 to allow the recovery of the tissue particles 71 collected by the filter 49 as will be discussed in more detail below. The mixer 65 (FIGS. 4B-4D), such as a static mixer, is releasably coupled to the port 45 to receive the gel 62 and isolated tissue particles 71 from the interior space 41 of the housing and to create a mixture 80 of gel 62 and tissue particles 71. A receiver 70 (FIGS. 4B-4D) is releasably coupled to the mixer 65 to receive the mixture 80 from the mixer 65 and to, for example, provide the mixture 80 to a surgical site.

In operation, as shown in FIGS. 1 and 4A-4D, the surgical blade 10 is brought into contact with a desired bodily tissue, such as synovial or adipose tissue (FIG. 1). The operator cuts a desired amount of tissue from the donor site using the blade 10. The vacuum source 90 aspirates fluid and the cut tissue through the aspiration lumen 16 of the inner tubular member 14 to the tissue collection device 40. During aspiration of the fluid and cut tissue, the port 45 in the housing 42 is closed (FIG. 4A), using, for example, a valve, stop, plug, or other suitable device 43. The filter 47 removes undesirable cut tissue from the fluid pathway, such as particles larger than, for example, about 0.6 mm to about 2.4 mm. After passing through the filter 47, the remainder of the fluid and cut tissue pass through the filter 48, which removes undesirable cut tissue from the fluid pathway, such as particles larger than, for example, about 0.6 mm to about 1 mm. The remainder of the fluid and cut tissue pass through the filter 49 where tissue particles 71 of a desired size, such as particles larger than, for example, about 0.5 mm to about 50 μm are isolated and/or retained on the filter 49. The remainder of the cut tissue and fluid volume pass through the tissue collection device 40 and are aspirated to the collection apparatus (not shown).

Following aspiration of the fluid and cut tissue, the inlet 44 of the housing 42 is closed off using, for example, a valve, stop, plug, or other suitable device 43a, the housing 40 is removed from the tubing 50, 52, and the receiver 70 and static mixer 65 are attached to the port 45, using, for example, a Luer Lock (not shown) or other suitable connector (FIG. 4B). The syringe 60 containing the gel 62 is coupled to the outlet 46, for example, by a Luer lock (not shown) or other suitable connection. The gel 62 is then injected into the housing 40 and through the filter 49 to mix with and expel the tissue particles 71 from the filter 49 (FIG. 4C). The expelled tissue particles 71 and the gel 62 pass through the interior space 41 of the housing 42 and are forced through the port 45 to the mixer 65 (FIG. 4C). The mixer 65 mixes the tissue particles 71 and the gel 62 to promote even distribution of the tissue particles 71 within the gel 62, creating a mixture 80, which flows into the syringe 70 (FIGS. 4C-4D). Once the desired volume of the mixture 80 is collected in the syringe 70, the operator removes the syringe 70 from the mixer 65 and attaches the plunger 70a of the syringe 70 (FIGS. 4c-d). The operator then applies the mixture 80 at a desired location, such as the surgical site shown in FIG. 1, or the mixture 80 can be placed onto a tissue scaffold or used for further processing.

An alternative implementation of a tissue harvesting assembly 200 is illustrated in FIGS. 5, 6, and 7A-7F. The tissue harvesting assembly 200 comprises a tissue collection device 140 and an introducer 160 (FIGS. 7E-7F), for example, a syringe, containing a suitable volume (e.g., about 1 ml) of gel 62. The tissue collection device 140 comprises a substantially cylindrical housing 142 having an inlet 44 and an outlet 46. The housing 142 comprises a lid 143 that is releasably coupled to the housing 142 using, for example mating threads (not shown), a friction fit, or other suitable connection.

Filtration devices, such as disc filters 147, 148 and a filter 149 having a substantially frusto-conical or basket configuration, are positioned within the housing 142, with filter 147 disposed closest to or adjacent the inlet 44, filter 149 disposed closest to or adjacent the outlet 46, and filter 148 disposed between filters 147 and 149. In particular, the filters 147, 148 are disposed within the lid 143, and the filter 149 is removably attached to an underside 143a of the lid 143, using, for example, threads (not shown), a friction fit, or other suitable connection. The housing 140 comprises one or more projecting ribs 145 (FIG. 6) disposed about the interior of the cylindrical housing 140. The ribs 145 are configured and shaped to receive the filter 149 and to releasably hold the filter 149, for example, by a friction fit, within the housing 140.

The filter 147 comprises a set of pores having a pore size of about 0.6 mm to about 2.4 mm, the filter 148 comprises a set of pores having a pore size of about 0.6 mm to about 1 mm, and the filter 149 comprises a set of pores having a pore size of about 0.5 mm to about 50 .mu.m. The filters 147 and 148 filter out larger tissue particles and allow smaller particles to pass through. The filter 149 then filters out particles 71 (FIG. 7B) of a desired size and allow particles smaller than the desired size to pass through. While two filters 147, 148 are shown, the tissue collection device 140 may comprise only one of the filters 147, 148 used in conjunction with the filter 149 to collect tissue particles 71 of a desired size.

The assembly 200 further comprises a container 170 defining a cavity 170a (FIGS. 7C-7F) configured and shaped to receive the filter 149 in a fluid-tight manner therein. An upper portion 170b of the container 170 is configured with threads, or other suitable mating connections, to receive the lid 143 of the housing 140 as will be described in more detail below.

The introducer 160 (FIGS. 7E-7F), for example, a syringe, contains a suitable volume (e.g., about 1 ml) of gel 62. The syringe 160 is used to mix the gel 62 with the tissue particles 71 to create a mixture 80 within the container 170, and thereafter, to aspirate the mixture 80 from the container 170.

Figure 5:
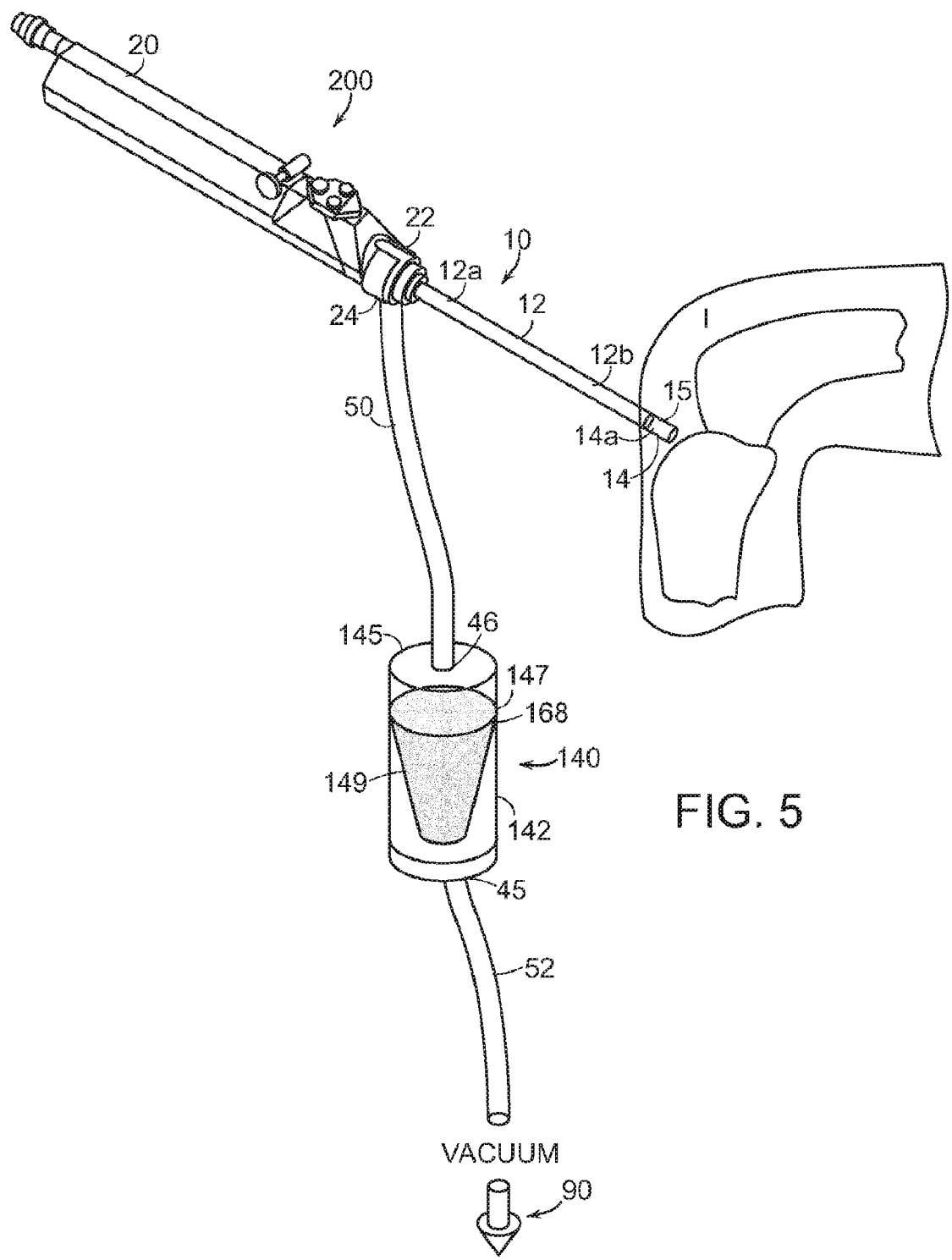
FIG. 5 is an illustration of an alternative tissue harvesting assembly shown in use.
Figure 6:
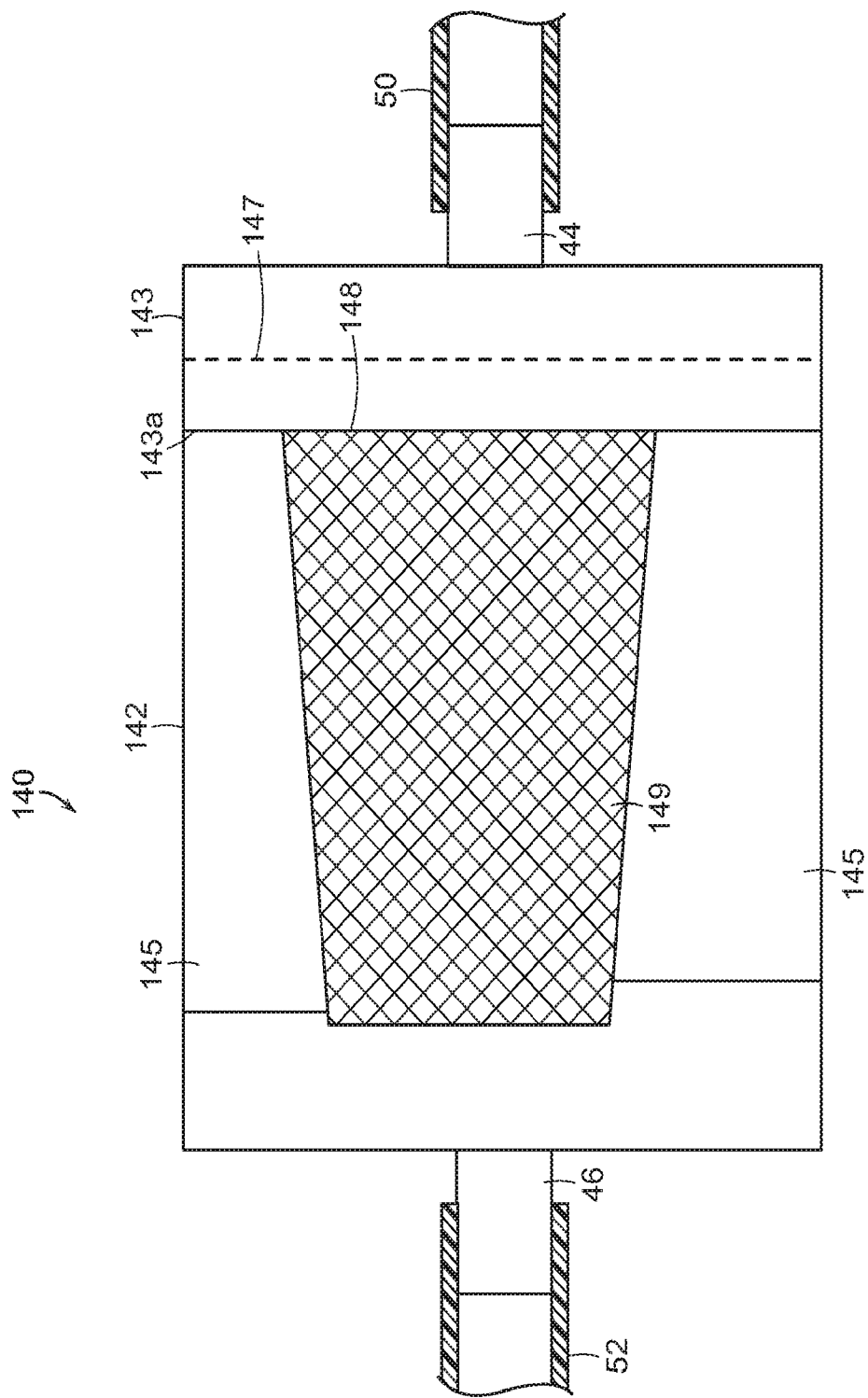
FIG. 6 is a cross-sectional view of a tissue collection apparatus of the assembly of FIG. 5.

In operation, as shown in FIGS. 5 and 7A-7F, the surgical blade 10 is brought into contact with a desired bodily tissue, such as synovial or adipose tissue (FIG. 5). The operator cuts a desired amount of tissue from the donor site using the blade 10. The vacuum source 90 aspirates fluid and the cut tissue through the aspiration lumen 16 of the inner tubular member 14 to the tissue collection device 140. During aspiration, the fluid and cut tissue flow through the filter 147, which removes undesirable cut tissue from the fluid pathway, such as particles larger than, for example, about 0.6 mm to about 2.4 mm. After passing through the filter 147, the remainder of the fluid and cut tissue pass through the filter 148, which removes undesirable cut tissue from the fluid pathway, such as particles larger than, for example, about 0.6 mm to about 1 mm. The remainder of the fluid and cut tissue pass through the filter 149 where tissue particles 71 (FIG. 7B) of a desired size, such as particles larger than, for example, about 0.5 mm to about 50 µm are isolated and/or retained on the filter 149. The remainder of the cut tissue and fluid volume pass through the tissue collection device 140 and are aspirated to the collection apparatus (not shown).

Following aspiration of the fluid and cut tissue, the lid 143, including the filters 147, 148, and 149, is removed from the housing 142 (FIG. 7B) and coupled to the upper portion 170b of the container 170 (FIG. 7C-7D). The cavity 170a receives the filter 149 in a fluid-tight manner, via, for example, a friction fit, between the filter 149 and the cavity 170a. Once the filter 149 is positioned in the container 170, the operator removes the lid 143, including the filters 147, 148, from the container 170, leaving the filter 149 within the cavity 170a of the container 170. For example, if the filter 149 is coupled to the lid 143, using a threaded connection and the lid 143 is coupled to the container 170 via a threaded connection, the two sets of threaded connections may be configured such that when the lid 143 is unscrewed from the container 170, the filter 149 is unscrewed from the lid 143. Alternatively, if, for example, the filter 149 is coupled to the lid 143 via a friction fit, then the cavity 170a of the container 170 is configured to provide a sufficient force to retain the filter 149 upon removal of the lid 143 from the container.

Once the lid 143 is removed from the container 170, the operator uses the syringe 160 to inject the gel 62 within the cavity 170a. The gel 62 mixes with the tissue particles 71 to form a mixture 80 of tissue and gel (FIG. 7E). The mixture 80 is then aspirated from the container 170 using the syringe 160 (FIG. 7F). Once the desired volume of the mixture 80 is collected in the syringe 160, the operator may apply the mixture 80 at a desired location, such as the surgical site shown in FIG. 5, or the mixture 80 can be placed onto a tissue scaffold or used as a feed for further processing.

Figure 8:
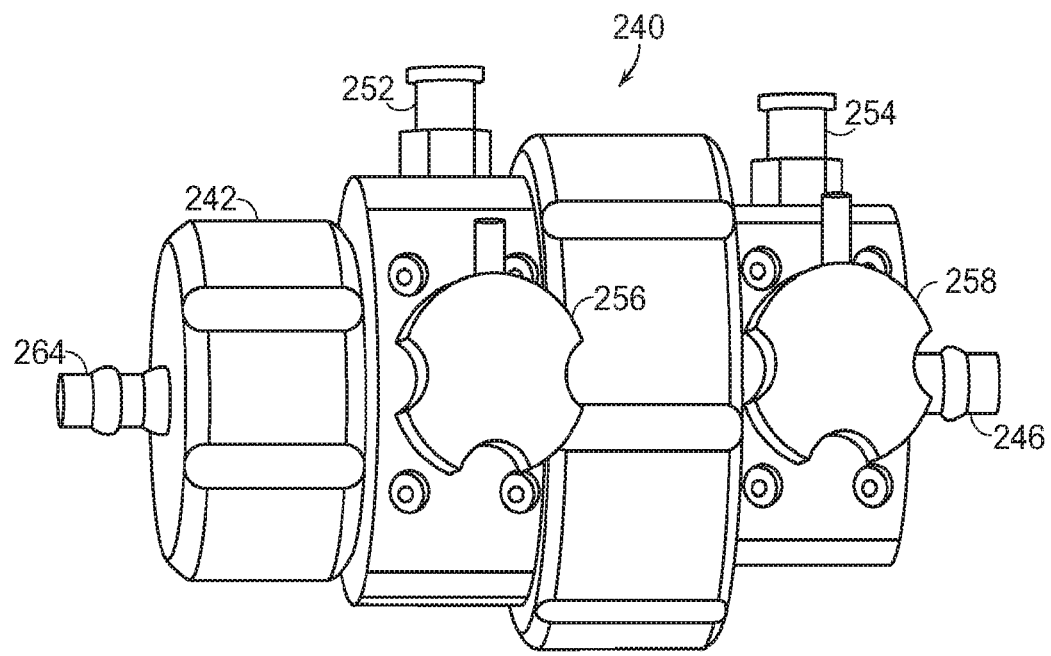
FIG. 8 is an illustration of an alternative implementation of the tissue collection apparatus of the assembly of FIG. 1.
Figure 9:
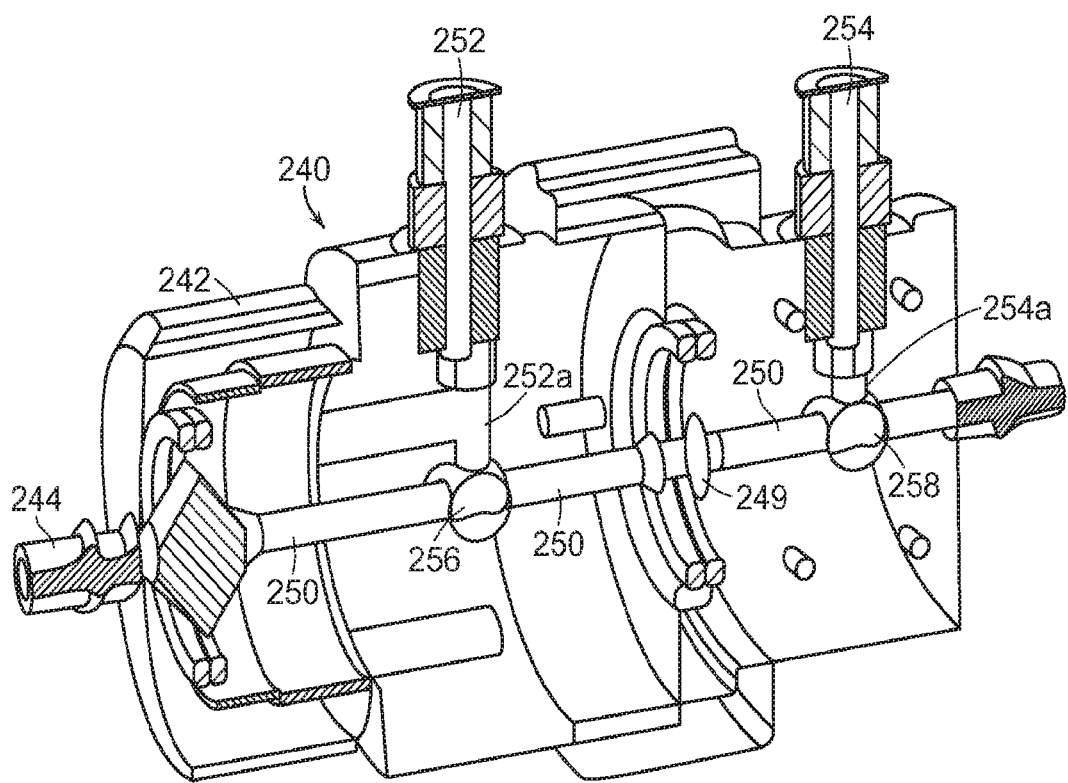
FIG. 9 is a cross-section view of the tissue collection apparatus of FIG. 8.

In an alternative implementation illustrated in FIGS. 8 and 9, a tissue collection device 240 comprises a housing 242 having an inlet 244 and an outlet 246. Positioned within the housing 242 are filters 247 and 249. Filter 247 is disposed adjacent the inlet 244 and filter 249 is disposed adjacent the outlet 246. Extending between the inlet 244 and the outlet 246 is a fluid-flow conduit 250 in fluid-flow communication with the inlet 244, the outlet 246 and the filters 247 and 249. The housing 242 further comprises ports 252 and 254 in fluid-flow communication with the conduit 250 via conduits 252a and 254a, respectively. At the intersections of conduits 250 and 252a and conduits 250 and 254a are three-way valves 256, 258, respectively, that control flow of fluid and tissue or cells between the inlet 244 and the outlet 246, and flow of gel and a mixture of gel and tissue or cells between the ports 252 and 254, as will be described in more detail below.

In the implementation shown in FIGS. 8 and 9, the filter 247 comprises a set of pores having a pore size in the range of about 0.6 mm to about 2.4 mm to allow particles smaller than the pore sizes to pass through the filter 247 and the filter 249 comprises a set of pores having a pore size of about 50 µm to about 0.5 mm to capture particles larger than about 50 µm in the filter 249.

In operation, the operator cuts a desired amount of tissue from a donor site using the surgical blade 10, as described above, and fluid and cut tissue are aspirated through the tissue collection device 240 via the inlet 244. During aspiration of the fluid and cut tissue, the ports 252 and 254 are closed to fluid flow by the three-way valves 256 and 258. The filter 247 removes undesirable cut tissue from the fluid pathway, such as particles in the range of larger than about 0.6 mm to about 2.4 mm. After passing through the filter 247, the fluid and cut tissue pass through the conduit 250 and through the filter 249 where tissue particles of a desired size, such as particles larger than, for example, about 0.5 mm to about 50 µm are isolated and/or retained on the filter 249. The remainder of the cut tissue and fluid volume pass through the tissue collection device 240 and are aspirated to a collection apparatus (not shown).

Following aspiration of the fluid and cut tissue, the inlet 244 of the housing 242 is closed off to fluid flow and the port 252 is opened to fluid flow using, for example, three-way valve 256. Likewise, the outlet 246 of the housing 242 is closed off to fluid flow and the port 254 is opened to fluid flow using, for example, three-way valve 258. The receiver 70, and optionally, the static mixer 65, discussed above, can then be attached to the port 252. The syringe 60 containing the gel 62 is then coupled to the port 254 and the gel 62 is injected into the housing 240 and through the filter 249 to mix with and expel the tissue particles (not shown) from the filter 249. The expelled tissue particles and gel 62 pass through the conduit 250 and are forced through the port 252 to, for example, the mixer 65 (FIG. 4C) and into the receiver 70 as described above.

In addition to being used in conjunction with the surgical blade assemblies described above, each of the tissue collection devices 40, 140, and 240 can be loaded with biological components by other methods. For example, cell pellets cultured in vitro can be aspirated (e.g. using a vacuum source) through one of the tissue collection devices 40, 140, 240 and then mixed with a biocompatible gel in the manner described above.

Figure 10:
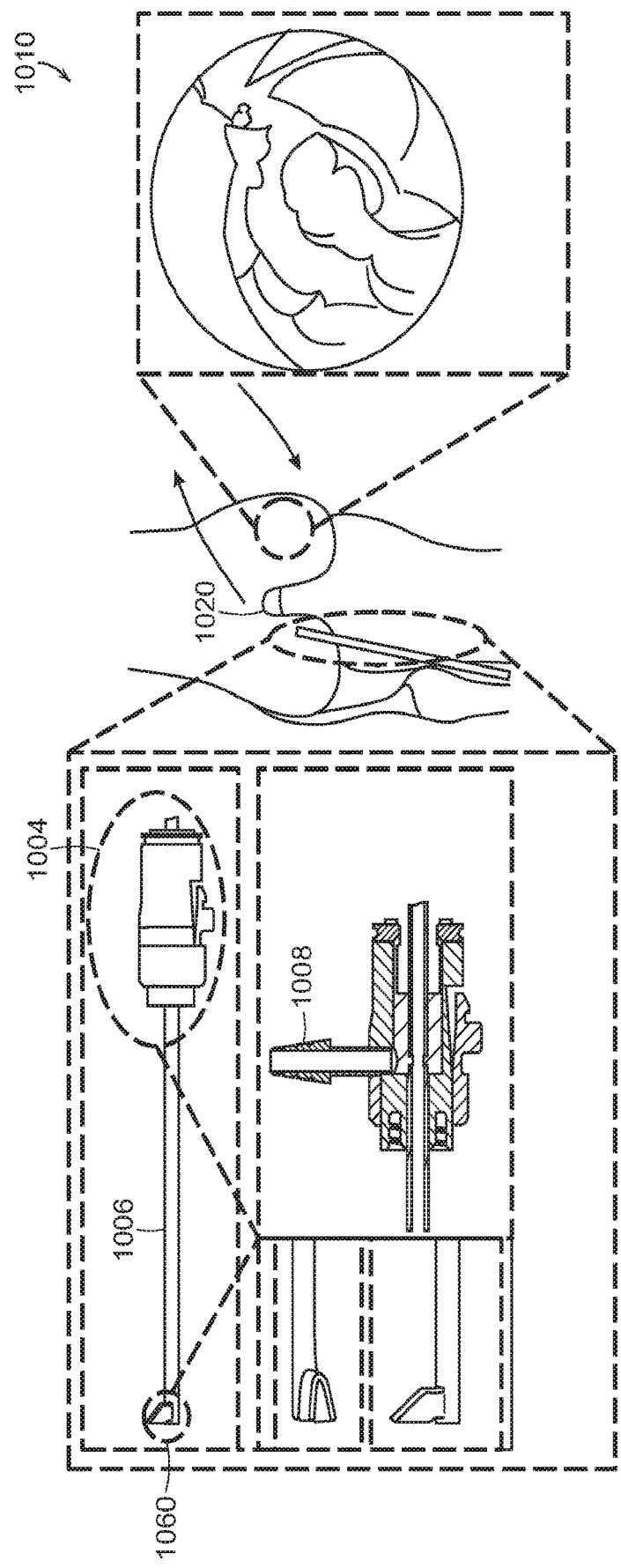
FIG. 10 is an illustration of a surgical technique using a tissue harvesting tool according to an aspect of the present disclosure.

Another aspect of the present disclosure includes a chondral autograft transfer system (CATS) tool configured to harvest, mince, and collect cartilage tissue. Referring to FIG. 10, the CATS tool includes a shaver blade and tissue collector combination device. According to aspects of the present disclosure, the CATS tool is configured to harvest and mince soft tissue such as the cartilage tissue which is then collected in the tissue collector. An example tissue collector according to an aspect of the present disclosure is shown in FIG. 12.

An illustrative embodiment of a CATS tool according to aspects of the present disclosure may be coupled to and functions in cooperation with an existing hand piece and power supply, such as the Dyonics hand piece and power supply.

In the illustrative embodiment, the CATS tool includes a shaver blade 1002 portion at a distal end a lumen 1006 and a hub 1004 at a proximal end of the lumen. The shaver blade 1002 of the CATS tool and the tissue collector portion (1200, FIG. 12) of the CATS tool may cooperatively be connected using standard plastic tubing. In one example, a hole is located on the side of the hub 1004 to facilitate fluid flow when an aspiration force is applied to the CATS tool. A barb 1008 is inserted into the hole to allow standard tubing to be attached to the modified blade. The barb 1008 directs an aspiration path from the hub to the tissue collector. According to an aspect of the present disclosure, additional holes are located on the sides of the lumen 1006 at the proximal end of the lumen within the hub 1004.

Under an aspiration force, fluid carrying the minced tissue is directed to flow out of the side port and into tubing (tubing not shown) leading to the tissue collector without having to pass through a conventional reusable handpiece (not shown) that attaches to a proximal end of the device. One end of a standard plastic tubing is installed onto the barb 1008. Referring to FIG. 12, the other end of the standard tubing is inserted onto the inflow portion 1202 of the tissue collector 1200 (FIG. 12). In this embodiment, additional standard plastic tubing is inserted onto the outflow portion 1204 of the tissue collector 1200, allowing waste to pass through the device and for disposal according to standard operating room protocol.

The tissue cutter portion 1100 of the CATS tool is described further with reference to FIGS. 11A and 11B. The tissue cutter portion 1100 includes a lumen 1101 that has an outer shaft 1106 and an inner shaft, which is rotatable within the outer shaft 1106. The outer shaft 1106 includes a first distal window (not shown) and the inner shaft has a second distal window (not shown). Edges of the first distal window and the second distal window cooperate to provide a cutting action there-between upon rotation of the inner shaft within the outer shaft 1106. A shaver blade 1103 is formed on a curette 1102 that extends from the outer shaft 1106 around the first window. The curette 1102 is attached to the distal end of the outer shaft 1106. This allows the device to dig into the smooth surface of the articular cartilage for tissue harvest like an open ring curette.

As the autologous tissue passes through the CATS tool, it is minced by shaver blade and cutting action of the first distal window and second distal window edges before being collected in the tissue collector 1200 (FIG. 12). The minced autologous tissue is then implanted into the cartilage defect 1010 (FIG. 10), and may be secured by a biomaterial such as fibrin, for example.

Referring to FIG. 12, the tissue collector 1200 includes an inflow portion 1202 of an outer housing and outflow portion 1204 of the outer housing. A filter portion 1206 is located inside the outer housing. The filter portion 1206 captures and collects the minced tissue fragments as they flow through the tissue collector 1200. Collection of tissue in a desired range of sizes is facilitated by pores in the filter portion 1206 that are smaller than the tissue fragments.

In one embodiment, the inflow portion 1202 and outflow portion 1204 are closed using a magnetic mechanism that allows for reversible opening and closing of the housing. The filter portion 1206 is reversibly removable from the outer housing.

During surgery, the cartilage defect site 1010 is prepared using standard techniques. This may involve removing damaged cartilage down to a bony layer, leaving behind a void space with clean vertical walls. This may be accomplished by mechanical debridement using curettes. In a second site 1020 separate from the cartilage defect site 1010, autologous cartilage tissue is harvested using the disclosed shaver blade-tissue collector combination device. The second site may be a low-load-bearing site, such as the intercondylar femoral notch or the superomedial or lateral trochlea. These are locations that are currently used to harvest tissue for other cartilage repair procedures like autologous chondrocyte implantation (ACI) and mosaicplasty, for example.

A method 1300 for using the disclosed CATS tool according to another aspect of the present disclosure is described with reference to FIG. 13. At block 1302, the method includes harvesting autologous cartilage tissue from a low-weight-bearing site of a patient. At block 1304, the method includes mincing the autologous cartilage tissue as it passes through the CATS tool. At block 1306, the method includes collecting the minced autologous cartilage tissue for implantation into a focal cartilage defect to enhance tissue repair by supplying an influx of viable cells. The disclosed method 1300 is similar to mosaicplasty, except the presently disclosed method treats chondral defects instead of osteochondral defects and implants cartilage fragments rather than osteochondral plugs. The harvested cartilage tissue can be secured in the cartilage defect. In an illustrative embodiment the harvested cartilage tissue is secured in the cartilage defect using a fibrin glue.

In alternative embodiments, the distal cutting end of the modified shaver blade may be modified, in various ways such as changing the angle of the curette, changing the window opening size and shape and/or changing diameters of the inner and outer pieces may be changed. In alternative embodiments, the tissue collector may also be modified. For example, the inner portion 1206 may be changed by varying the pore sizes, which would affect the size of the minced tissue that would be captured/collected by the tissue collector.

In an alternative embodiment, the minced tissue may be seeded in or onto a cartilage scaffold product prior to implantation in the cartilage lesion. The cartilage scaffold may be a porous sponge-like biomaterial, such as a collagen scaffold, or a gel-like biomaterial, such as alginate. The cartilage scaffold could be used in place of, or in conjunction with, fibrin, for example.

According to an aspect of the present disclosure the mincing feature of the disclosed apparatus can be turned off, i.e. by stopping rotation of the inner shaft relative to the outer shaft. This facilitates harvesting and collection of larger strips of cartilage tissue for reimplantation. The subchondral bone in the cartilage defect site may optionally undergo microfracture prior to implantation of the minced cartilage tissue, which is currently accomplished using picks, awls, and drill bits.

A number of implementations of the disclosure have been described. Nevertheless, it will be understood that various modifications may be made without departing from the spirit and scope of the disclosure. For example, while the tissue collection devices 40, 140, 240 have been described as coupled to the blade 10 via a flexible tubing 50, the devices 40, 140, 240 could be directly coupled to, for example, the port 24 of the blade 10 (see FIGS. 1 and 5). In addition, although the tissue collection devices 40, 140, 240 have been described as including substantially cylindrical housings 42, 142, and 242, respectively, housings 42, 142, and 242 could be any suitable shape. Further, although the syringes 60, 160 have been described as containing a volume of about 1 ml of a biocompatible gel 62, the syringes 60, 160 could contain more or less of the gel 62 depending on the size of the defect to be treated.

In addition, rather than using a static mixer with the tissue collection device 40 to promote a more even distribution of the tissue particles 71 in the gel 62, the mixture 80 of gel 62 and tissue particles 71 may be realized solely within the interior space 41 of the housing 42, and the syringe 70 can be directly coupled to the port 45 to recover the mixture 80 directly from the interior space 41 of the housing 42. Further, rather than mixing the gel and tissue in a separate container, such as container 170, the outlet 46 of the tissue collection device 140 can be plugged or otherwise sealed and the mixture 80 of gel 62 and tissue particles 71 can be realized directly in the tissue collective device 140.

Moreover, although the filtration devices have been described as either disk-shaped or basket-shaped filters, other suitable filtration devices having any number of possible geometric shapes may be employed. Such examples comprise nucleated cell, microfiltration, tubular, or hollow fiber filtration devices, having, for example, square, cylindrical, tubular, or round geometries. In addition, any filtration surface that contacts any of the relevant compositions of the tissue, fluid, or other surgical materials is sterile or can be readily sterilized.

For the purposes of this disclosure, the injectable gel 62 may comprise any suitable biological or synthetic gels. For example, the gel can comprise hyaluronic acid, alginate, cross-linked alginate, collagen, fibrin glue, fibrin clot, poly (N-isopropulacrylamide), agarose, chitin, chitosan, cellulose, polysaccharides, poly(oxyalkylene), a copolymer of poly(ethylene oxide)-poly(propylene oxide), poly(vinyl alcohol), polyacrylate, Matrigel, or blends thereof.

The apparatuses and systems described herein may be considered disposable, although they may be reused upon sterilization, such as by gamma irradiation, ethylene oxide, formalin, hydrogen peroxide, or sodium hypochlorite. The filters and syringes discussed herein may be commercially obtained. In particular implementations, the apparatus and components may be plastic, metal, or other suitable material.

Rather than the tubing connector 29 (FIG. 2) being in communication with the aspiration lumen 16 of the inner tubular member 14 via the chamber 26, the tubing connector 29 could be directly coupled to the inner tubular member 14. The tubing connector 29 can be coupled to the side port 24 using any suitable form of connection, including glue, weld, press fit, or, alternatively, the tubing connector 29 can be formed as one piece with the hub 22. The tubing connectors described herein can be made from plastic, metal, or any other suitable materials.

In addition, although the tissue harvesting assembly has been described as including a surgical blade 10 used to cut or resect bodily tissue, such as soft tissue, the tissue harvesting assembly can comprise an apparatus containing a curette or burr, for example, to remove bodily tissue, such as bone tissue.

According to another aspect of the present disclosure, a cartilage repair technique employs a shaver/cutter and tissue trap combination device to harvest cartilage tissue from a low-weight bearing site of a subject. Tissue that is shaved by the shaver blade is aspirated through a lumen of the tissue cutter.

A tissue collection apparatus as shown in FIGS. 14-17 is coupled in the aspiration path of the cutting via flexible aspiration tubing. The tissue collection apparatus includes a moveable porous disc having pores that are sized to allow tissue particles that are below a desired size to pass through and aspirated as waste tissue from the device. Tissue particles having at least the desired size are collected on the porous disc. The tissue collection apparatus includes an inflow chamber and an outflow chamber magnetically attached to a central housing portion. The porous disc is contained in the central housing portion. The inflow chamber and the outflow chamber can easily be removed from the central housing portion during surgery to access the collected tissue particles on the porous disc.

According to this aspect of the present disclosure, after a desired quantity of tissue is collected on the porous disc, the inflow chamber is removed from the central housing portion. A first plunger having a diameter matching the inside diameter of the central housing portion is then inserted into the inflow end of the central housing portion to compress all of the collected tissue against the porous disk. The first plunger is then removed and the outflow chamber is removed from the central housing portion. A second plunger is inserted into the outflow end of the central housing portion to push the porous disk and compressed tissue toward the inflow end of the central housing portion. In the disclosed embodiment, the first plunger and second plunger are formed on opposite ends of a single shaft.

The porous disk is pushed to a level that is flush with the inflow end of the central housing portion. This allows all of the collected tissue to be smoothly scraped from the central housing portion. The collected cartilage tissue particles can then be introduced to the cartilage repair site of the subject during the surgery and secured to a cartilage defect, possibly by using a fibrin glue.

The apparatus to harvest, mince, and collect cartilage tissue according to this aspect of the present disclosure includes a shaver blade that uses a hand piece such as the Dyonics model hand-piece by Smith & Nephew of London, UK, a power supply, and a moveable tissue trap for collection and autologous transfer of cartilage tissue.

Resected cartilage tissue is captured in a tissue trap that allows for autologous transfer. The tissue trap is mobile and works in conjunction with a plunger to compact and pass collected cartilage into a focal chondral defect. Using the disclosed apparatus, autologous cartilage tissue is harvested from a low-weight-bearing site, minced as it passes through the device, and then collected for implantation into a focal cartilage defect to enhance tissue repair by supplying an influx of viable cells.

Figure 14:
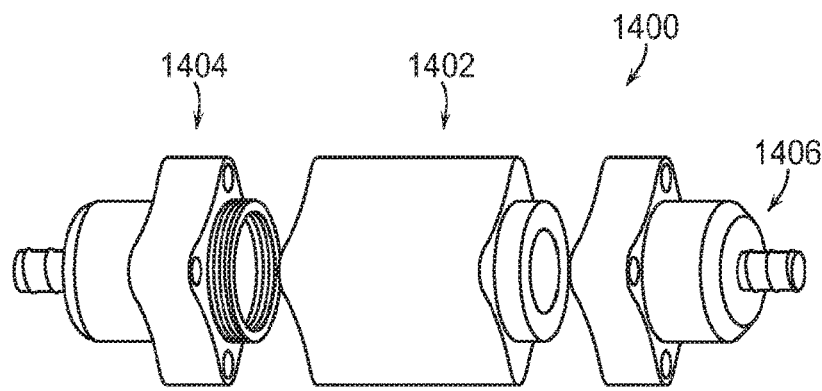
FIG. 14 is an exploded view of a tissue collector portion of the tissue harvesting tool according to an aspect of the present disclosure.

An exploded view of disclosed tissue trap is shown in FIG. 14. This tissue trap 1400 may be connected to the disclosed modified shaver blade with standard ¼" plastic tubing. The tubing is connected to the inflow chamber of the tissue trap and passes collected cartilage using suction.

Figure 15:
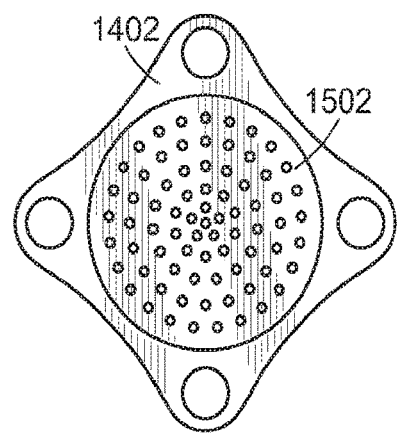
FIG. 15 is an illustration of a porous disc installed in a tissue collector portion of the tissue harvesting tool according to an aspect of the present disclosure.

Referring to FIG. 15, the tissue trap 1400 contains a moveable porous disc 1502. The pores of this moveable disc 1502 are sized to allow cartilage fragments of a desired size to be collected. The fragments below the desired size are aspirated out to waste through standard ¼" plastic tubing using suction and disposed of per standard operating room protocol. In an illustrative embodiment, the components are magnetically held together to allow for sufficient suction.

Figure 16:
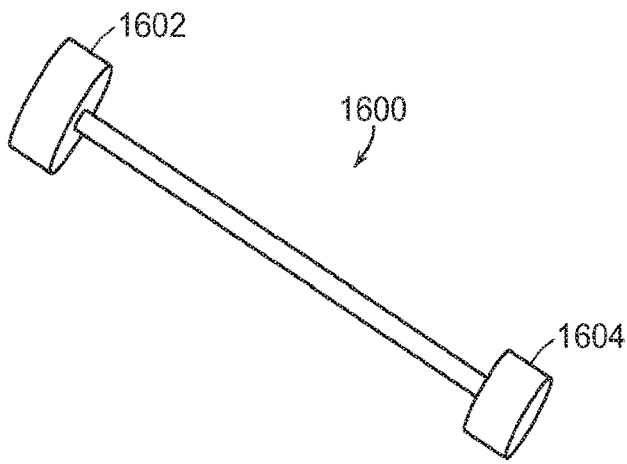
FIG. 16 is an illustration of a plunger used in conjunction with a tissue collector portion of the tissue harvesting tool according to an aspect of the present disclosure.
Figure 17:
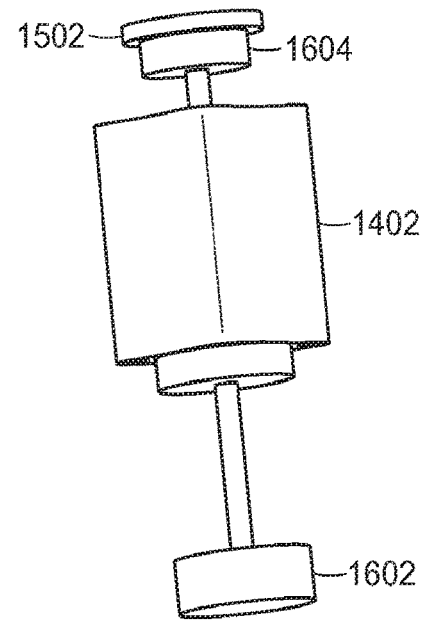
FIG. 17 is an illustration of a tissue plunger installed through a central body portion of a tissue collector in the tissue harvesting tool according to an aspect of the present disclosure.

This tissue trap works in conjunction with a plunger 1600, as pictured in FIGS. 16-17. After collection of tissue in the tissue trap 1400, the in-flow chamber 1404 is removed. The large end 1602 of the plunger 1600 is passed into the central housing portion 1402 to compress the cartilage to form a disc. Next, the out-flow chamber 1406 is removed from the central housing portion 1402. The smaller end 1604 of the plunger 1600 is then used to push the filter along with the captured tissue particles from the out-flow end so that the filter is externally flush.

The porous disc 1502 sits within the central housing portion 1402. The pores are sized such that a tissue particles smaller than a desired size will pass through and be aspirated out to waste. The porous disc 1502 sits flush with the inner body of the central housing portion 1402 so as to capture all possible cartilage.

The porous disc 1502 slides into the central housing portion 1402. In an illustrative embodiment, a magnetic mechanism is located inside the housing and chambers. The magnetic mechanism is functional to removably couple the inflow chamber and the outflow chamber to the housing.

The collection of cartilage tissue fragments on the porous disc 1502 allows the cartilage to be easily transferred back into a chondral defect. The porous disc 1502 is contained within a central housing portion 1402.

The central housing portion 1402 is sized and configured to allow for ease of use for the plunger 1600. The central housing portion 1402 contains two openings. One opening of the housing is removably coupled to the inflow chamber 1404. The other opening of the central housing portion 1402 is removably coupled to the outflow chamber 1406. In an illustrative embodiment, the opening that couples to the inflow chamber 1404 has a diameter of about 1.22 inches, and the opening that couples to the outflow chamber 1406 has a diameter of about 0.96 inches. This sizing allows for the porous disc 1502 to sit comfortably within the central housing portion 1402.

In the illustrative embodiment, the plunger 1600 is sized differently on either end. A larger end 1602 of the plunger 1600 is sized to pass easily through the large opening in the central housing portion 1402 while making contact with the inner housing wall. This is to ensure that any tissue particles that collect on the walls of the central housing portion 1402 are compressed into a disc. An opposite smaller end 1604 of the plunger is sized to pass easily through the smaller opening in the central housing portion 1402. This is to ensure that after collection, the plunger 1600 is able to move the porous disc 1502 and tissue toward the larger opening. The tissue trap 1400 is held in a vertical orientation during these procedures so as not to lose any collected tissue fragments.

The surgical procedure is detailed as follows. At the time of surgery, the cartilage defect is prepared using standard technique. This entails removing the damaged cartilage down to the bony layer, leaving behind a void space with clean vertical walls. This is usually accomplished by mechanical debridement using curettes.

In a second site separate from the cartilage defect site, autologous cartilage tissue is harvested using the shaver blade/tissue trap combo device. The second site is a low-loadbearing site, such as the intercondylar femoral notch or the superomedial or lateral trochlea, locations that are currently used to harvest tissue for other cartilage repair procedures like autologous chondrocyte implantation (ACI) and mosaicplasty, for example.

As the autologous tissue passes through the device, it is minced by the device and then collected in the tissue trap. After collection in the tissue trap, the plunger compacts and then elevates the tissue out of the filter. The minced autologous tissue can then be mixed with autologous blood to promote the tissue particles to stick together. This blood/tissue particle solution can then be passed through a cannula into a focal chondral defect.

According to other aspects of the present disclosure, various aspects of the tissue collector may be modified. For example, the porous disc may be changed, by varying the pore sizes according to a desired size of the minced tissue to be captured and collected by the tissue collector. The mechanism to hold the components of the tissue trap may be changed, for example by introducing threads to allow the pieces to twist together as opposed to magnetically held together. The components could also be press-fit together, for example.

The collected tissue may be combined with a biomaterial such as fibrin to hold the particles together. The tissue could be seeded on/in a cartilage scaffold product prior to implantation in the cartilage lesion; for example. The cartilage scaffold could be a porous sponge-like biomaterial, such as a collagen scaffold, or a gel-like biomaterial, such as alginate. The cartilage scaffold could be used in place of, or in conjunction with, fibrin.

The filter can be modified such that autologous blood is combined with the fragments within the housing. The surface of the filter or the inner housing wall can be etched to promote thrombosis when in contact with autologous blood. Plasma spraying can also be considered to promote thrombosis in the presence of autologous blood. The subchondral bone in the cartilage defect site can optionally undergo microfracture or exposure to ablation treatment prior to implantation of the minced cartilage tissue.

An apparatus for tissue collection, according to another aspect of the present disclosure includes a central housing portion comprising an inflow end and an outflow end, an inflow chamber removably coupled to the inflow end of the central housing portion, and an outflow chamber removably coupled to the outflow end of the central housing portion. The inflow chamber defining a high pressure space within the apparatus, and the outflow chamber defining a low pressure space within the apparatus.

The central housing portion includes a removable filter separating the high pressure zone from the low pressure zone. The removable filter includes pores sized to allow fluid to pass through the pores and to prevent cut tissue fragments from passing through the pores. The removable filter is separable from the inflow chamber and the outflow chamber.

According to an aspect of the present disclosure, the apparatus also includes a plunger having a diameter configured for pushing the removable filter toward the inflow end of the central housing portion. According to this aspect of the present disclosure, the removable filter includes a constant shape in cross section such that the removable filter is configured to be pushed out of the central housing portion by a plunger when the inflow chamber and the outflow chamber are separated from the central housing portion. For example, the removable filter may be shaped as a disk or a cylinder.

According to another aspect of the present disclosure, a tissue cutter is coupled in fluid communication with the inflow chamber. In an illustrative embodiment, the tissue cutter includes a lumen having a proximal end and distal end. The lumen is configured in an aspiration path of the apparatus and includes an outer shaft and an inner shaft. The tissue cutter also includes a hub coupled to the proximal end of the lumen. A cutter portion is formed on the distal end of the lumen. The cutter portion includes a first window in the outer shaft cooperative with a second window of the inner shaft. Edges of the first distal window and the second distal window are configured to cooperate in a cutting action there-between upon rotation of the inner shaft within the outer shaft.

A method for collecting tissue according to another aspect of the present disclosure includes applying fluid pressure across a collection device from an inflow chamber defining a high pressure zone of the collection device to an outflow chamber defining a low pressure zone of the collection device. A central housing is removably coupled between the inflow chamber and the outflow chamber. The method includes collecting cut tissue fragments on a removable filter in the collection device. The removable filter separates the high pressure zone from the low pressure zone.

In an illustrative embodiment, the method includes separating the inflow chamber and the outflow chamber from the collection device and inserting a plunger through the collection device while the inflow chamber and the outflow chamber are separated from the collection device such that the plunger forces the removable filter and the tissue from the collection device. The plunger has a diameter configured for pushing the removable filter toward the inflow end. The removable filter has a constant shape in cross section such that the removable filter is configured to be pushed out of the collection device by a plunger when the inflow chamber and the outflow chamber are separated from the collection device. For example, the removable filter may have a disk shape or a cylinder shape.

According to another aspect of the present disclosure, the method also includes coupling the inflow chamber to an aspiration path of a tissue cutter. In an illustrative embodiment, the tissue cutter includes a lumen having a proximal end and distal end. The lumen is configured in the aspiration path of the apparatus and including an outer shaft and an inner shaft. A hub is coupled to the proximal end of the lumen and a cutter portion is formed on the distal end of the lumen. The cutter portion includes a first window in the outer shaft cooperative with a second window of the inner shaft. Edges of the first distal window and the second distal window are configured to cooperate in a cutting action there-between upon rotation of the inner shaft within the outer shaft.

A system for tissue collection according to an aspect of the present disclosure includes a central housing portion having an inflow end, an outflow end and a shell defining cylindrical space between the inflow end and the outflow end. An inflow chamber is removably coupled to the inflow end of the central housing portion, and an outflow chamber is removably coupled to the outflow end of the central housing portion. A slidable porous filter is located within the cylindrical space. In an illustrative embodiment, the filter has pores sized for retaining filtering cut tissue fragments having at least predetermined size and the filter has a diameter configured for matching the cylindrical space. The filter may have a disk shape, for example.

The system also includes a first plunger configured for pushing the porous filter toward the inflow end of the central housing portion. In an illustrative embodiment, the system also includes a plunger shaft coupled to the first plunger; and a second plunger coupled to the plunger shaft. The second plunger has a diameter configure for matching the cylindrical space and compressing the cut tissue fragments against the porous filter.

These aspects of the present disclosure provides a one-stage autologous healing solution for cartilage repair to be performed arthroscopically or as a mini-open procedure. For sports medicine knee surgeons, the disclosed method utilizes a cost effective orthopedic tool that collects minimally manipulated autologous viable cartilage cells/tissue that can be re-implanted into the patient. In the future, this product concept may be further developed by combining with a cartilage scaffold to provide an advanced orthobiologic solution for improved cartilage repair compared to microfracture.

An advantage of this technique is the ability to avoid multiple surgeries, to avoid non-arthroscopic surgeries and to improve long-term biochemical and biomechanical properties of the reparative tissue by efficiently harvesting and implanting autologous tissue during a single surgical procedure.

To evaluate the feasibility of a novel device to harvest and collect autologous minced cartilage which can be used for the single stage repair of articular cartilage defects. A novel device was created to resect and collect autologous particulated cartilage. The aim of this study was to determine if mincing cartilage can influence chondrocyte behavior. Biochemical assays and histological assessments were used to determine cell viability and chondrogenic potential.

Bovine knees were sourced from abattoirs. Cartilage was resected from the lateral trochlear groove or intercondylar notch using a novel device and collected in an inline tissue trap. Various versions of the device were used to create resected fragments with varying sizes. The collected fragments were allocated and transferred to 12-well NetWell plates with cell culture media containing FBS and no growth factors. NetWells of the appropriate pore size were used in order to allow expanded chondrocytes to pass through and adhere to the base of the plate while maintaining the fragments themselves above the base of the plate. Cartilage fragments were cultured for various timepoints (t=0, 7, 14, 21 days) with media changes three times a week and appropriate passaging. At each timepoint the expanded cells were trypsinized and cultured in micromass for another 3 weeks to evaluate chondrogenic potential. After the 3 weeks, the cultured micromasses were allocated for biochemical assays or histological assessment. Chondrogenic potential was determined using the DMMB assay to quantify s-GAG content. Cell viability was determined using the Picogreen assay to quantify DNA content. Comparisons between groups were based on a normalized sGAG:DNA ratio to determine approximate ECM production per cell. Cultured micromasses were also fixed, sectioned and stained with Hematoxylin and Eosin (H&E) as a general stain and Safranin-O for s-GAG content.

A correlation between the size of the collected fragments and chondrocyte migration and expansion was noted. Smaller fragments showed increased chondrocyte migration and expansion from the fragments over three weeks. Small fragments (<1 mm2) had higher chondrocyte expansion (~1,000,000 cells) than that of large fragments; (1.5±0.5 mm2; ~500,000 cells) over three weeks. Cultured Micromasses from small fragments had significantly higher sGAG:DNA (0.039) than that of large fragments (0.025) (P=0.034). Staining of Micromass cultures revealed cells that were rounded and resided in lacunae, typical characteristics of chondrocyte morphology, and intense positive staining with Safranin-O, indicating the presence of sGAG.

Mincing cartilage to create particulated cartilage fragments improves chondrocyte migration and expansion from the fragments. This is likely due to the greater surface area of the particulated cartilage which improves cell migration from the cartilage matrix. Smaller fragment sizes correlated to greater cell expansion and increased ECM production of the cells which migrated out of the cartilage fragments. Cell viability of the cells retained in the particulated fragments was also maintained over three weeks. These results demonstrate the feasibility of a novel device to harvest and collect autologous minced cartilage. This device shows promise as a new technology to be used for single stage repair of articular cartilage defects.

Accordingly, other embodiments are within the scope of the following claims.

What is claimed is:

1. A system for tissue collection, comprising:
   a handpiece having a proximal end, a distal end, and a longitudinal axis extending therebetween;
   a tubular member coupled to the distal end of the handpiece configured for aspirating tissue;
   a tissue collection device coupled to the handpiece by a flexible tube extending from the handpiece such that the tissue collection device is spaced apart from the handpiece and no portion of the tissue collection device extends along the longitudinal axis into the flexible tube, the tissue collection device comprising:
      a central housing portion comprising an inflow end, an outflow end, and a lumen located between the inflow end and the outflow end; and
      a filter coupled to the lumen, the filter having pores sized for retaining cut tissue fragments having at least a predetermined size;
      an inflow chamber at the inflow end of the central housing portion;
      an outflow chamber at the outflow end of the central housing portion; and
   a plunger having a geometry configured for matching the lumen and shifting a position of the cut tissue fragments.

2. The system of claim 1, wherein the filter comprises a cylinder shape.

3. The system of claim 1, wherein the filter comprises a disc shape.

4. The system of claim 1, further comprising a tissue cutter in fluid communication with the central housing portion, the tissue cutter positioned at a distal end of the tubular member.

5. The system of claim 4, wherein the tissue cutter comprises:
   a cutter lumen having a proximal end and distal end, the lumen configured in the tubular member, the tubular member including an outer shaft and an inner shaft;
   a hub coupled to the proximal end of the cutter lumen;
   a cutter portion formed on the distal end of the cutter lumen, the cutter portion including a first window in the outer shaft cooperative with a second window of the inner shaft.

6. The system of claim 5, wherein edges of the first distal window and the second distal window are configured to cooperate in a cutting action there-between upon rotation of the inner shaft within the outer shaft.

7. The system of claim 1, wherein the plunger comprises a first circular end portion, a second circular end portion opposite the first circular end portion, and a cylindrical rod extending between the first and second end portions, a diameter of the cylindrical rod selected to be smaller than a diameter of both of the first and second circular end portions.

* * * * *